United States Patent [19]

Soula

[11] Patent Number: 4,479,022

[45] Date of Patent: Oct. 23, 1984

[54] ISOMERIZATION OF BROMOHALOGENOBENZENES

[75] Inventor: Gerard Soula, Meyzieu, France

[73] Assignee: Rhone-Poulenc Specialites Chimiques, Courbevoie, France

[21] Appl. No.: 365,994

[22] Filed: Apr. 6, 1982

[30] Foreign Application Priority Data

Apr. 8, 1981 [FR] France ............................... 81 07026

[51] Int. Cl.$^3$ ............................................. C07C 17/24
[52] U.S. Cl. .................................... 570/202; 570/143; 570/151
[58] Field of Search ......................... 570/202, 143, 151

[56] References Cited

U.S. PATENT DOCUMENTS 3,742,073  6/1973  Bacha et al. ......................... 570/202
4,347,390  8/1982  Nishiyama et al. .................. 570/202

FOREIGN PATENT DOCUMENTS 43303  1/1982  European Pat. Off. ............ 570/202

OTHER PUBLICATIONS

Bunnett & Moyer, JACS, [93:5], Mar. 10, 1971, pp. 1183-1190.
Bunnett & Scorrano, JACS, [93:5], Mar. 10, 1971, pp. 1190-1197.

*Primary Examiner*—Charles F. Warren
*Assistant Examiner*—Joseph A. Boska
*Attorney, Agent, or Firm*—Burns, Doane, Swecker & Mathis

[57] ABSTRACT

Bromohalogenobenzenes are isomerized to useful, e.g., pharmaceutical or phytosanitary intermediates, by contacting the same with an alkaline base and a catalyst compound which forms a complex with the cation of said alkaline base.

37 Claims, No Drawings

ISOMERIZATION OF BROMOHALOGENOBENZENES

BACKGROUND OF THE INVENTION

1. Field of the Invention

The present invention relates to the isomerization of bromohalogenobenzenes.

2. Description of the Prior Art

The isomerization of bromohalogenobenzenes is generally known to this art. Thus, published French Patent Application No. 2,362,807 describes the preparation of 1-bromo-3,5-dichlorobenzene by isomerization of 1-bromo-2,4-dichlorobenzene at 80°–180° C. in the presence of an aluminum halide, such as anhydrous $AlCl_3$. Such process exhibits several disadvantages, however, which render its industrial application precarious. In fact, concurrently formed are numerous isomers of the desired product, i.e., 2,3-dichlorobromobenzene, 2,5-dichlorobromobenzene, 3,4-dichlorobromobenzene and 2,6-dichlorobromobenzene, while the product of industrial interest is 3,5-dichlorobromobenzene, a known intermediate for the facile preparation of 3,5-dichloroaniline. Thirdly, it will also be appreciated that in the subject process various dismutation products (dichlorobenzenes and dichlorodibromobenzenes) too are prepared. Accordingly, upon completion of the subject reaction, highly complex reaction mixtures result which can be separated into the individual components thereof only upon carrying out lengthy and costly separation processes. A last disadvantage that should also be mentioned is that elevated temperatures must be maintained in order to complete the reaction successfully.

Compare also Moyer & Bunnett, *J.A.C.S.* p. 1891, June 20, 1963, which describes the preparation of 1-bromo-3,5-dichlorobenzene from 1-bromo-2,4-dichlorobenzene in the presence of potassium anilide in liquid ammonia. The yields obtained by this process are very low (33%) and, in practice, preclude any industrial application thereof.

Therefore, serious need exists in this art for a process for the isomerization of bromohalogenobenzenes which enables the selective production of desired product under conditions of mild temperatures and also the ready recovery of final product while at the same time avoiding the use of solvents, the industrial handling of which is precarious and dangerous.

SUMMARY OF THE INVENTION

Accordingly, a major object of the present invention is the provision of such improved process for the isomerization of bromohalogenobenzenes, and one which conspicuously avoids those disadvantages and drawbacks above outlined.

Briefly, the present invention features a process for the isomerization of bromohalogenobenzenes, comprising contacting (i) a bromohalogenobenzene having the structural formula:

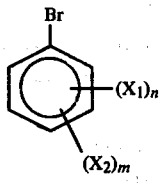

wherein $X_1$ and $X_2$, which may be the same or different, each represents a chlorine or a fluorine atom, and n and m are numbers greater than or equal to 0 and less than or equal to 3, with the sum of n+m being equal to 2 or 3, with (ii) an alkaline base and (iii) at least one compound which effects complexation of the cation of said alkaline base.

DETAILED DESCRIPTION OF THE INVENTION

More particularly according to this invention, and in a first preferred embodiment thereof, the compound which forms a complex with the cation of the alkaline base is a macrocyclic polyether having 15 to 30 atoms in the ring structure and comprising 5 to 10 —O—X units, wherein X is either —$CHR_1$—$CHR_2$— or —$CHR_1$—$CHR_4$—$CHR_3R_2$, and wherein $R_1$, $R_2$, $R_3$ and $R_4$, which may be the same or different, are each a hydrogen atom or an alkyl radical having 1 to 4 carbon atoms, with the proviso that one X may be —$CHR_1$—$CHR_4$—$CR_3R_2$— when the —O—X units are otherwise —O—$CHR_1$—$CHR_2$— radicals.

In a second preferred embodiment of the invention, the compound which forms a complex with the cation of the alkaline base is a macrocyclic or bicyclic compound having the structural formula Ia or Ib:

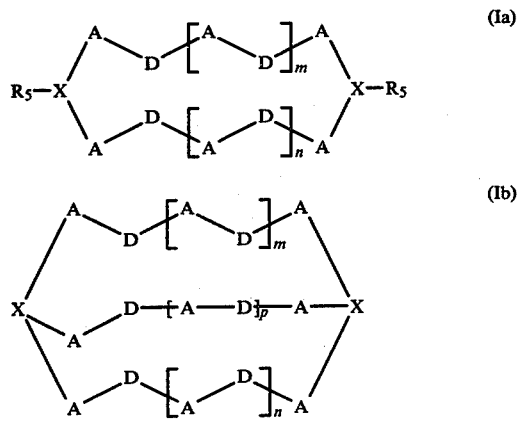

wherein X is N or P, A is an alkylene radical having from 1 to 3 carbon atoms, D is O, S or N—$R_6$, wherein $R_6$ is an alkyl radical having from 1 to 6 carbon atoms, $R_5$ is an alkyl radical having from 1 to 6 carbon atoms, and n, m and p, which may be the same or different, are numbers ranging from 1 to 5.

And in a third preferred embodiment of the invention, the compound which forms a complex with the cation of the alkaline base is a tertiary amine having the structural formula:

$$N-[CHR_7-CHR_8-O-(CHR_9-CHR_{10}-O)_s-R_{11}]_3 \quad (II)$$

wherein s is a number preferably greater than or equal to 0 and less than or equal to 10 (0≦s≦10), $R_7$, $R_8$, $R_9$ and $R_{10}$, which may be the same or different, are each a hydrogen atom or an alkyl radical having from 1 to 4 carbon atoms and $R_{11}$ is an alkyl or cycloalkyl radical having from 1 to 12 carbon atoms, a phenyl radical or a —$C_qH_{2q}$—φ or $C_qH_{2q+1}$—φ— radical, wherein q ranges from 1 to 12 and φ is phenyl.

In yet a fourth preferred embodiment of the invention, the compound which forms a complex with the cation of the alkaline base is a linear polyether having the structural formula:

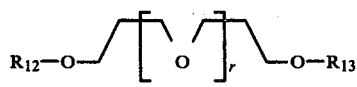

(III)

wherein r preferably ranges from 1 to 10 and wherein $R_{12}$ and $R_{13}$, which may be the same or different, each represents an alkyl radical having from 1 to 12 carbon atoms.

The macrocyclic polyethers which may be utilized consistent herewith are generally known to this art under the generic designation "crown ethers" and are described, for example, in published French Patent Application No. 2,026,481.

Exemplary of the crown ethers that can be used pursuant to this invention, representative are:

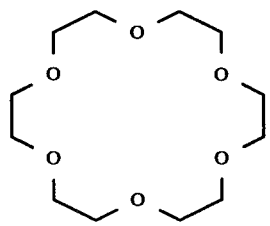

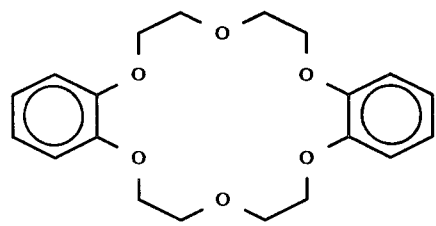

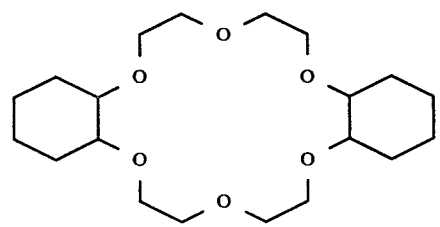

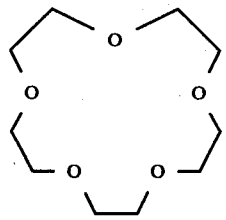

The macrocyclic and bicyclic compounds having the structural formulae Ia and Ib are described, for example, in published French Patent Application No. 2,052,947. Exemplary of such compounds suitable for use in the process according to the invention, the following are representative:

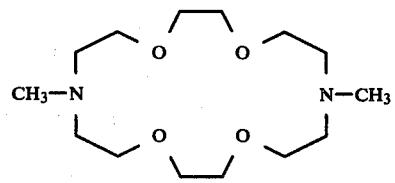

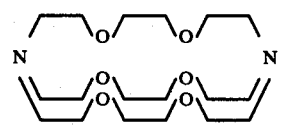

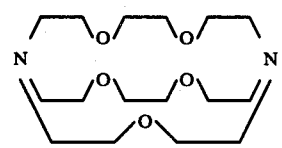

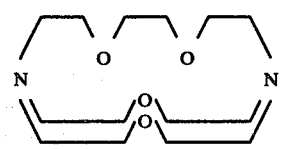

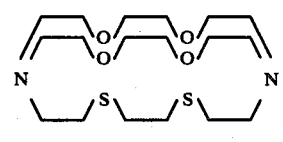

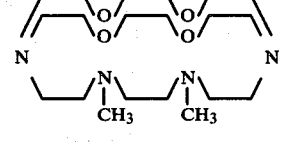

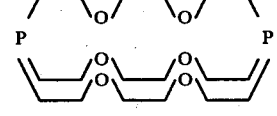

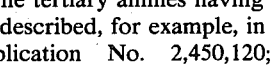

The tertiary amines having the structural formula II are described, for example, in published French Patent Application No. 2,450,120; French Patent No. 1,302,365.

The preferred tertiary amines of Formula II are those wherein $R_7$, $R_8$, $R_9$ and $R_{10}$ are each a hydrogen atom or a methyl radical and $R_{11}$ and s are as above defined.

Among such preferred tertiary amines, it is even more particularly preferred to employ those in which s is greater than or equal to 0 and less than or equal to 6 and $R_{11}$ represents an alkyl radical having from 1 to 4 carbon atoms.

The following tertiary amines having the structural Formula II are noted as illustrative:

[1] tris-(3-oxaheptyl)-amine of the formula:

$$N + CH_2-CH_2-O-C_4H_9)_3,$$

[2] tris-(3,6-dioxaheptyl)-amine of the formula:

$$N + CH_2-CH_2-O-CH_2-CH_2-O-CH_3)_3,$$

[3] tris-(3,6,9-trioxadecyl)-amine of the formula:

$$N + CH_2-CH_2-O-CH_2-CH_2-O-CH_2-CH_2-O-CH_3)_3,$$

[4] tris-(3,6-dioxaoctyl)-amine of the formula:

$$N + CH_2-CH_2-O-CH_2-CH_2-O-C_2H_5)_3,$$

[5] tris-(3,6,9-trioxaundecyl)-amine of the formula:

$$N + CH_2-CH_2-O-CH_2-CH_2-O-CH_2-CH_2-O-C_2H_5)_3,$$

[6] tris-(3,6-dioxanonyl)-amine of the formula:

$$N + CH_2-CH_2-O-CH_2-CH_2-O-C_3H_7)_3,$$

[7] tris-(3,6,9-trioxadodecyl)-amine of the formula:

$$N + CH_2-CH_2-O-CH_2-CH_2-O-CH_2-CH_2-O-C_3H_7)_3,$$

[8] tris-(3,6-dioxadecyl)-amine of the formula:

$$N + CH_2-CH_2-O-CH_2-CH_2-O-C_4H_9)_3,$$

[9] tris-(3,6,9-trioxatridecyl)-amine of the formula:

$$N + CH_2-CH_2-O-CH_2-CH_2-O-CH_2-CH_2-O-C_4H_9)_3,$$

[10] tris-(3,6-dioxa-4-methylheptyl)-amine of the formula:

$$N + CH_2-CH_2-O-CH(CH_3)-CH_2-O-CH_3]_3$$

and

[11] tris-(3,6-dioxa-2,4-dimethylheptyl)-amine of the formula:

$$N + CH_2-CH(CH_3)-O-CH(CH_3)-CH_2-O-CH_3]_3.$$

The preferred polyethers having the structural Formula III are those in which r ranges from 1 to 4 and $R_{12}$ represents an alkyl radical having from 1 to 6 carbon atoms.

The following are representative of the polyethers having the structural Formula III which can be employed in the process of the present invention:

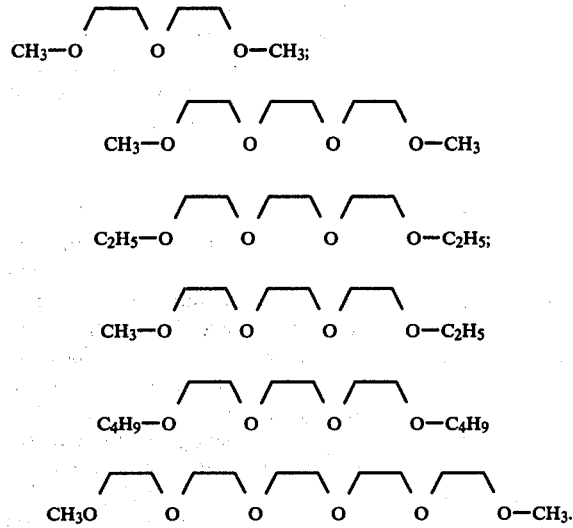

Moreover, the aforesaid representative compounds may be used singly or in any admixture thereof.

The alkaline base employed in the process of the invention is preferably selected from among the alkaline amides. More particularly, sodium, potassium or lithium amides are the preferred.

The following compounds are exemplary of the bromohalogenobenzene starting materials which may be employed in the process according to the invention (the final products prepared therefrom are noted in parentheses):

2,4-dichlorobromobenzene (3,5-dichlorobromobenzene);
2,3-dichlorobromobenzene (3,4-dichlorobromobenzene);
2,3,4-trichlorobromobenzene (3,4,5-trichlorobromobenzene);
2,4-difluorobromobenzene (3,5-difluorobromobenzene);
2,3-difluorobromobenzene (3,4-difluorobromobenzene);
2,4-difluoro-3-chlorobromobenzene (3,5-difluoro-4-chlorobromobenzene); and 2,3,4-trifluorobromobenzene (3,4,5-trifluorobromobenzene).

The invention is especially desirable in light of the products formed, in cases where the starting material is 2,4-dichlorobromobenzene, 2,3-dichlorobromobenzene or 2,4-difluorobromobenzene.

The reaction may be effected in the presence of absence of an inert solvent. In the first case, an aprotic, apolar or an aprotic, slightly polar solvent is used, such as, for example, toluene, chlorobenzene, tetrahydrofuran, dioxane or ethylene glycol dimethyl ether.

The process is preferably carried out at a temperature ranging from 0° to 60° C. and preferably from 10° to 40° C.

The alkaline base is used in quantities such that the molar ratio of the alkaline base to the bromohalogenobenzene starting material preferably ranges from 0.05 to 1, and more preferably from 0.05 to 0.5.

The molar ratio of the compound which forms the complex with the cation of the alkaline base to the bromohalogenobenzene starting material preferably ranges from 0.005 to 0.2, and more preferably from 0.01 to 0.1.

The process according to the invention is conveniently carried out at atmospheric pressure, although pressures greater or lower than atmospheric remain within the scope of the invention.

In order to further illustrate the present invention and the advantages thereof, the following specific examples are given, it being understood that same are intended only as illustrative and in nowise limitative.

EXAMPLE 1

Isomerization of 2,4-dichlorobromobenzene:

Into a 500 ml, four-necked reaction vessel equipped with a mechanical agitator, a thermometer, a nitrogen inlet and a dropping funnel (itself equipped with a mechanical agitator), there were successively introduced, under a stream of nitrogen, 169 g anhydrous chlorobenzene, 113 g 2,4-dichlorobromobenzene (0.5 mole) and 8.1 g tris-(3,6-dioxaheptyl)-amine (0.025 mole). The mixture was agitated and subsequently, over the course of about one hour, 6 g sodium amide were added as a suspension in 6 g of toluene by means of the dropping funnel. Agitation was continued for one hour upon completion of the addition of the amide and then 8 g ammonium chloride were added to neutralize the sodium amide.

The reaction mixture was then washed with 100 cm$^3$ of a 10% aqueous hydrochloric acid solution, then decanted and dried on silica gel.

The chlorobenzene was removed and the products distilled. In this manner, 2.6 g meta-dichlorobenzene, 97 g dichlorobromobenzenes consisting of 78% 3,5-dichlorobromobenzene and 22% 2,4-dichlorobromobenzene were recovered.

EXAMPLES 2 TO 5

Isomerization of 2,4-dichlorobromobenzene

Into a 20 ml reaction vessel equipped with a condenser and placed under a stream of nitrogen, 1.6 g chlorobenzene, 1.13 g 2,4-dichlorobromobenzene (5 mmoles), 0.1 g sodium amide (1.3 mole) as a suspension in 0.1 g toluene and a catalyst in a concentration varying from 5 to 10 molar %, were successively introduced. The reaction mixture was agitated at 20° for a predetermined period of time, then analyzed by gaseous phase chromatography. The results obtained as a function of the catalyst employed and the time of reaction, are reported in Table 1.

COMPARATIVE EXAMPLE

The immediately above example was repeated, but without the addition of a catalyst. After 3 hours, the amount of starting material converted was zero.

EXAMPLE 6

Isomerization of 2,3-dichlorobromobenzene

Into a 50 ml reaction vessel equipped with a condenser and placed under a stream of nitrogen, 6.8 g chlorobenzene, 2.26 g 2,3-dichlorobromobenzene (0.01 mole), 0.22 g sodium amide dispersed in 0.22 g toluene and 0.32 g tris-(3,6-dioxahexyl)amine (0.0028 mole), were successively introduced. The reaction mixture was agitated for 2 hours at 21° C., then analyzed by gaseous phase chromatography. The amount of the 2,3-dichlorobromobenzene isomerized was 42% and the reaction yield was 92%.

EXAMPLE 7

Isomerization of 2,4-difluorobromobenzene

Into a 50 ml reaction vessel equipped with a cooling means and a magnetic stirrer, 19.3 g 2,4-difluorobromobenzene (0.1 mole), 4.6 g toluene and 1.6 g tris-(3,6-dioxaheptyl)-amine (0.005 mole), were successively introduced. The reaction mixture was cooled to 10° C. under a blanket of nitrogen, then 0.19 g sodium amide (0.005 mole) as a suspension in 0.2 g toluene was added. After 20 minutes of reaction under agitation, the reaction mixture obtained consisted of 79% 3,5-difluorobromobenzene and 21% 2,4-difluorobromobenzene. The mixture was distilled: 12.1 g 3,5-difluorobromobenzene were recovered ($\theta = 140°$ C.).

TABLE I

| Example | Catalyst (molar %) | Reaction time | Amount of 3,5-dichlorobromobenzene converted (%) | Yield |
|---|---|---|---|---|
| 2 | Cryptand (2,2,2)* (5%) | 30 min | 84 | 70 |
| 3 | Crown ether** dicyclohexyl 18 C.6 (5%) | 30 min | 82 | 94 |
| 4 | Triethylene glycol dimethyl ether (10%) | 3 hour | 70 | 90 |
| 5 | Tris-(3,6-dioxaheptyl)-amine (5%) | 1 hour | 80 | 94 |

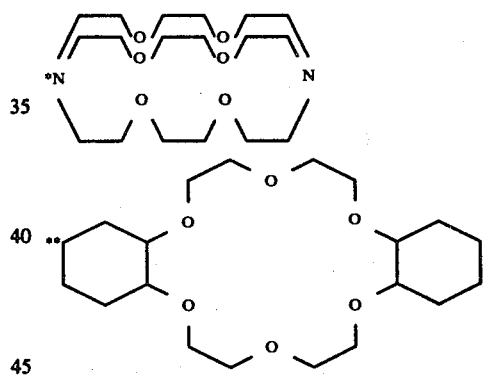

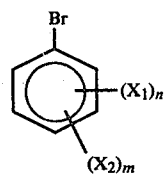

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims.

What is claimed is:

1. A process for the isomerization of a bromohalogenobenzene, comprising contacting (i) a bromohalogenobenzene having the structural formula:

wherein $X_1$ and $X_2$, which may be the same or different, are each a chlorine or fluorine atom, and n and m are numbers greater than or equal to 0 and less than or equal to 3, with the sum of n+m being equal to 2 or 3, with (ii) an alkaline base and (iii) at least one catalyst compound which forms a complex with the cation of said alkaline base, said compound (iii) which forms a complex with the cation of the alkaline base is a linear polyether having the structural formula:

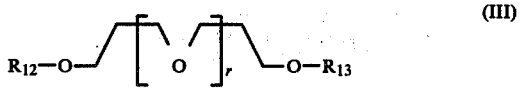

wherein r ranges from 1 to 10 and wherein $R_{12}$ and $R_{13}$, which may be the same or different, each represents an alkyl radical having from 1 to 12 carbon atoms.

2. The process as defined by claim 1, wherein said linear polyether having the structural formula (III), r ranges from 1 to 4 and $R_{12}$ is an alkyl radical having from 1 to 6 carbon atoms.

3. The process as defined by claim 1, said linear polyether having the structural formula (III) being:

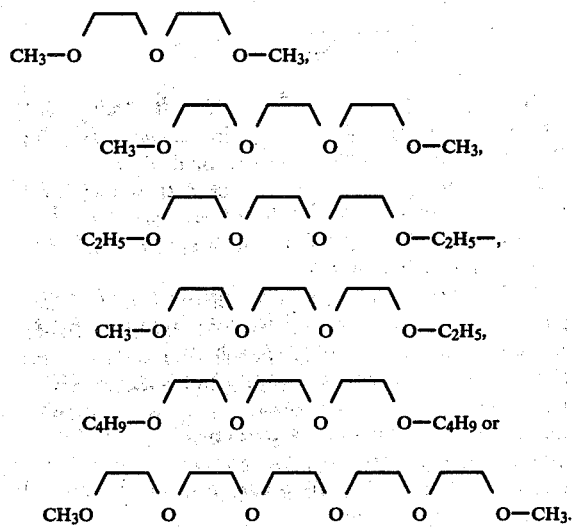

4. The process as defined by claim 1, said alkaline base (ii) being an alkaline amide.

5. The process as defined by claim 4, said alkaline amide being sodium, lithium or potassium amide.

6. The process as defined by claim 1, said bromohalogenobenzene (i) being 2,4-dichlorobromobenzene, 2,3-dichlorobromobenzene, 2,3,4-trichlorobromobenzene, 2,4-difluorobromobenzene, 2,3-difluorobromobenzene, 2,4-difluoro-3-chlorobromobenzene or 2,3,4-trifluorobromobenzene.

7. The process as defined by claim 1, said isomerization being carried out in an aprotic, apolar or an aprotic, slightly polar solvent.

8. The process as defined by claim 1, said isomerization being carried out in toluene, chlorobenzene, tetrahydrofuran, dioxane or ethylene glycol dimethyl ether.

9. The process as defined by claim 1, wherein the molar ratio of the alkaline base (ii) to the bromohalogenobenzene starting material (i) ranges from 0.05 to 1.

10. The process as defined by claim 9, said molar ratio ranging from 0.05 to 0.5.

11. The process as defined by claim 9, wherein the molar ratio of the compound (iii) which forms the complex with the cation of the alkaline base to the bromohalogenobenzene starting material (i) ranges from 0.005 to 0.2.

12. The process as defined by claim 11, said molar ratio ranging from 0.01 to 0.1.

13. The process as defined by claim 1, said isomerization being carried out at a temperature ranging from about 0° to 60° C.

14. The process as defined by claim 13, said temperature ranging from about 10° to 40° C.

15. A process for the isomerization of a dichlorobromobenzene, comprising contacting (i) a dichlorobromobenzene with (ii) an alkaline base and (iii) at least one catalyst compound which forms a complex with the cation of said alkaline base.

16. The process as defined by claim 15, wherein said compound (iii) which forms a complex with the cation of the alkaline base is a macrocyclic polyether having 15 to 30 atoms in the ring structure and comprising 5 to 10 —O—X units, wherein X is either —CHR$_1$—CHR$_2$— or —CHR$_1$—CHR$_4$—CHR$_3$R$_2$, and wherein R$_1$, R$_2$, R$_3$ and R$_4$, which may be the same or different, are each a hydrogen atom or an alkyl radical having 1 to 4 carbon atoms, with the proviso that one X may be —CHR$_1$—CHR$_4$—CR$_3$R$_2$— when the —O—X units are otherwise —O—CHR$_1$—CHR$_2$— radicals.

17. The process as defined by claim 15, wherein said compound (iii) which forms a complex with the cation of the alkaline base is a macrocyclic or bicyclic compound having the structural formula Ia or Ib:

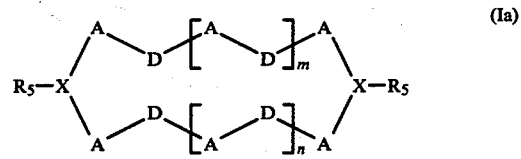

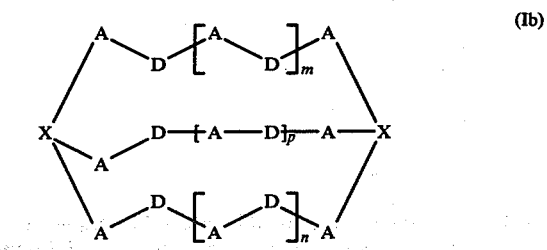

wherein X is N or P, A is an alkylene radical having from 1 to 3 carbon atoms, D is O, S or N—R$_6$, wherein R$_6$ is an alkyl radical having from 1 to 6 carbon atoms, R$_5$ is an alkyl radical having from 1 to 6 carbon atoms, and n, m and p, which may be the same or different, are numbers ranging from 1 to 5.

18. The process as defined by claim 15, wherein said compound (iii) which forms a complex with the cation of the alkaline base is a tertiary amine having the structural formula:

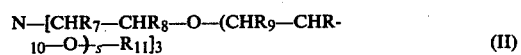

wherein s is a number greater than or equal to 0 and less than or equal to 10, R$_7$, R$_8$, R$_9$ and R$_{10}$, which may be the same or different, are each a hydrogen atom or an alkyl radical having from 1 to 4 carbon atoms and R$_{11}$ is an alkyl or cycloalkyl radical having from 1 to 12 carbon atoms, a phenyl radical or a —$C_qH_{2q}$—$\phi$ or $C_qH_{2q+1}$—$\phi$— radical, wherein q ranges from 1 to 12 and $\phi$ is phenyl.

19. The process as defined by claim 16, said macrocyclic polyether having one of the following structural formulae:

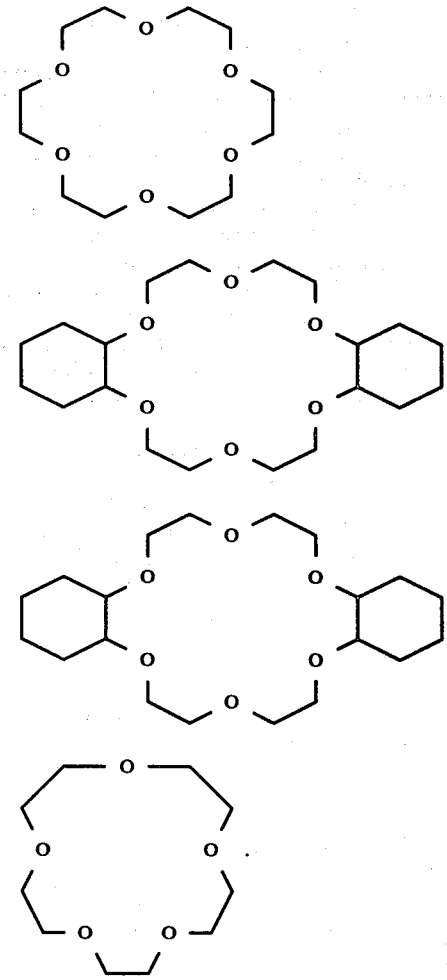

20. The process as defined by claim 17, said macrocyclic or bicyclic compound having one of the following structural formulae:

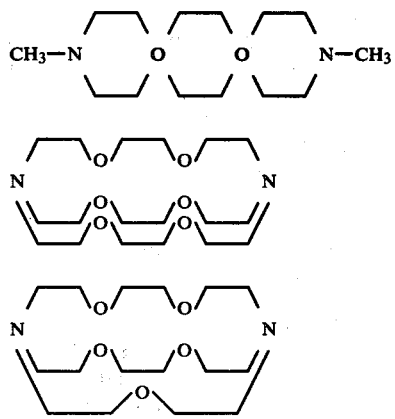

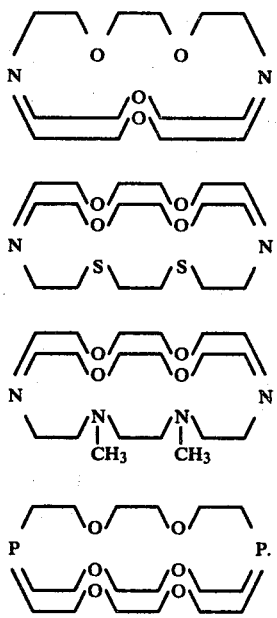

21. The process as defined by claim 18, wherein said tertiary amine having the structural formula (II), $R_7$, $R_8$, $R_9$ and $R_{10}$ are each hydrogen or methyl.

22. The process as defined by claim 21, wherein said tertiary amine having the structural formula (II), s ranges from 0 to 6 and $R_{11}$ is an alkyl radical having from 1 to 4 carbon atoms.

23. The process as defined by claim 18, said tertiary amine having the structural formula (II) being tris-(3-oxaheptyl)-amine, tris-(3,6-dioxaheptyl)-amine, tris-(3,6,9-trioxadecyl)-amine, tris-(3,6-dioxaoctyl)-amine, tris-(3,6,9-trioxaundecyl)-amine, tris-(3,6-dioxanonyl)-amine, tris-(3,6,9-trioxadodecyl)-amine, tris-(3,6-dioxadecyl)-amine, tris-(3,6,9-trioxatridecyl)-amine, tris-(3,6-dioxa-4-methylheptyl)-amine, or tris-(3,6-dioxa-2,4-dimethylheptyl)-amine.

24. The process as defined by claim 15, wherein said compound (iii) which forms a complex with the cation of the alkaline base is a linear polyether having the structural formula:

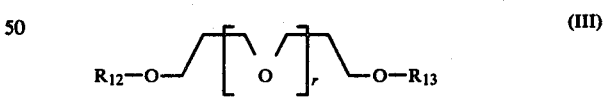

(III)

wherein r ranges from 1 to 10 and wherein $R_{12}$ and $R_{13}$, which may be the same or different, each represents an alkyl radical having from 1 to 12 carbon atoms.

25. The process as defined by claim 24, wherein said linear polyether having the structural formula (III), r ranges from 1 to 4 and $R_{12}$ is an alkyl radical having from 1 to 6 carbon atoms.

26. The process as defined by claim 24, said linear polyether having the structural formula (III) being:

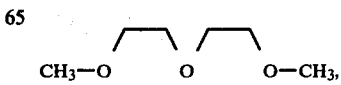

-continued

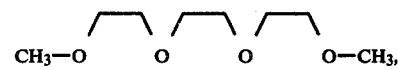

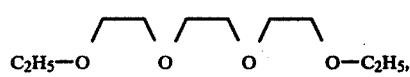

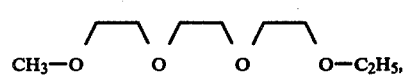

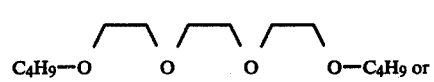

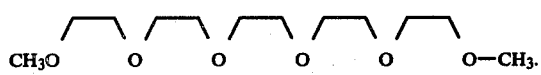

27. The process as defined by claim 15, said alkaline base (ii) being an alkaline amide.

28. The process as defined by claim 27, said alkaline amide being sodium, lithium or potassium amide.

29. The process as defined by claim 15, said dichlorobromobenzene (i) being 2,4-dichlorobromobenzene or 2,3-dichlorobromobenzene.

30. The process as defined by claim 15, said isomerization being carried out in an aprotic, apolar or an aprotic, slightly polar solvent.

31. The process as defined by claim 15, said isomerization being carried out in toluene, chlorobenzene, tetrahydrofuran, dioxane or ethylene glycol dimethyl ether.

32. The process as defined by claim 15, wherein the molar ratio of the alkaline base (ii) to the dichlorobromobenzene starting material (i) ranges from 0.05 to 1.

33. The process as defined by claim 32, said molar ratio ranging from 0.05 to 0.5.

34. The process as defined by claim 32, wherein the molar ratio of the compound (iii) which forms the complex with the cation of the alkaline base to the dichlorobromobenzene starting material (i) ranges from 0.005 to 0.2.

35. The process as defined by claim 34, said molar ratio ranging from 0.01 to 0.1.

36. The process as defined by claim 15, said isomerization being carried out at a temperature ranging from about 0° to 60° C.

37. The process as defined by claim 36, said temperature ranging from about 10° to 40° C.

* * * * *